US006969452B2

(12) United States Patent
He et al.

(10) Patent No.: US 6,969,452 B2
(45) Date of Patent: Nov. 29, 2005

(54) TWO-DIMENSIONAL PROTEIN SEPARATIONS USING CHROMATOFOCUSING AND MULTIPLEXED CAPILLARY GEL ELECTROPHORESIS

(75) Inventors: Yan He, Ames, IA (US); Ho-Ming Pang, Ames, IA (US); Siquan Luo, Ames, IA (US); Futian Han, Ames, IA (US)

(73) Assignee: Combisep, Inc., Ames, IA (US)

( * ) Notice: Subject to any disclaimer, the term of this patent is extended or adjusted under 35 U.S.C. 154(b) by 315 days.

(21) Appl. No.: 10/377,909

(22) Filed: Feb. 28, 2003

(65) Prior Publication Data

US 2004/0168915 A1 Sep. 2, 2004

(51) Int. Cl.[7] .................... G01N 27/447; G01N 27/453
(52) U.S. Cl. ...................... 204/451; 204/452; 204/601
(58) Field of Search .............................. 204/451–455, 204/601–605; 422/70; 73/61.52; 436/161; 210/656, 660

(56) References Cited

U.S. PATENT DOCUMENTS

| 5,011,914 | A | 4/1991 | Collins et al. |
| 5,316,630 | A | 5/1994 | Dasgupta |
| 6,013,165 | A | 1/2000 | Wiktorowicz et al. |
| 2002/0033336 | A1 | 3/2002 | Liu et al. |
| 2002/0098595 | A1 | 7/2002 | Lubman et al. |
| 2002/0153252 | A1 | 10/2002 | Akins, Jr. |
| 2003/0089605 | A1 | 5/2003 | Timperman |

FOREIGN PATENT DOCUMENTS

| EP | 0 517 370 A1 | 9/1992 |

OTHER PUBLICATIONS

"Chromatofocusing," (Frey et al., Encyclopedia of Life Sciences, 2001, Nature Publishing Group) dowloaded from www.userpages.umbc.edu/~dfrey1/articles/els.pdf on Mar. 4, 2005.*
Vincentrelli et al., "Characterisation of each isoform of a F(ab')2 by capillary electrophoresis," Journal of Chromatography (1993), 641(2), 383-90).*
CAPLUS abstract of Rodriguez de Cordoba et al. Journal of Immunological Methods (1984), 69(2), 165-72.*
Lauzurica, P., et al. "Olive (*Olea Europea*) Pollen Allergens—II. Isolation and Characterization of Two Major Antigens" XP-002289345; Molecular Immunology, vol. 25, No. 4, pp 337-344, 1988.
Sluyterman et al., "Ten Years of Chromatofocusing: A Discussion", Journal of Chromatorgraphy, 470 (1989) pp. 317-326.
Shieh et al., "Capillary Sodium Dodecyl Sulfate Gel Electrophoresis of Proteins I. Reproducibility and Stability", Journal of Chromatography A. 676 (1994) pp. 219-226.
Liu et al., "Gradient Chromatofocusing High-performance Liquid Chromatography II. Theoretical Aspects", Journal of Chromatography, A. 762 (1997) pp. 47-54.
Logan et al., "A Simple, Two-Component Buffer Enhances Use of Chromatofocusing for Processing of Therapeutic Proteins", Biotechnology and Bioengineering, vol. 62, Jan 20, 1999.

(Continued)

*Primary Examiner*—Alex Noguerola
(74) *Attorney, Agent, or Firm*—McKee, Voorhees & Sease, P.L.C.

(57) ABSTRACT

Disclosed is a two-dimensional protein separation method. It makes separating a protein sample by chromatofocusing into a plurality of aliquots, and then loading each aliquot into a separate capillary tube; and separating each aliquot by multiplexed capillary electrophoresis to produce a two-dimensional array of separated proteins. A preferred integrated buffer for this system is also disclosed.

3 Claims, 3 Drawing Sheets

OTHER PUBLICATIONS

Weber et al., "Counterbalancing Hydrodynamic Sample Distortion Effects Increases Resolution of Free-flow Zone Electrophoresis", Electrophroesis, 19, pp. 1104-1109.

Gagnon, P., "Chromatofocusing: Does it Really Stack Up as a Process Tool?", Validated Biosystems Quarterly, 1999.

Chong et al., "Chromatofocusing Nonporous Reversed-phase High-performance Liquid Chromatorgraphy/electrospray Ionization Time-of-flight Mass Spectrometry of Proteins from Human Breast Cancer Whole Cell Lysates: a Novel Two-Dimensional Liquid Chromatography/mass Spectrometry Method", Rapid Communications in Mass Spectrometry, 2001; vol. 15, pp. 291-296.

Kang et al., "Chromatofocusing Using Micropellicular Column Packings with Computer-aided Design of the Elution Buffer Composition", Analytical Chemistry, vol. 74, No. 5, Mar. 1, 2002.

Shan et al., "Gradient Chromatofocusing. Versatile pH Gradient Separation of Proteins in Ion-Exchange HPLC: Characterization Studies", Analytical Chemistry, vol. 74, No. 21, Nov. 1, 2002.

http://www.aber.ac.uk/~mpgwww/Proteome/Tut 2D.html; Dr. James R. Jeffries. Institute of Biological Sciences, University of Wales at Aberystwyth, pp. 1-24, date printed Jan. 16, 2003.

http://ntri.tamuk.edu/chromatofocusing/joel.html; Natural Toxins Research Center at Texas A&M University, Kingsville, date printed Jan. 12, 2003.

* cited by examiner

TWO-DIMENSIONAL PROTEIN SEPARATIONS USING CHROMATOFOCUSING AND MULTIPLEXED CAPILLARY GEL ELECTROPHORESIS

TECHNICAL FIELD OF THE INVENTION

This invention relates to a chromatofocusing and multiplexed capillary gel electrophoresis system for the two-dimensional separation of proteins and to a method of using it.

BACKGROUND OF THE INVENTION

Protein mixtures can be difficult to resolve using only one separation technique. Therefore, two-dimensional or multi-dimensional separations are sometimes used. Two-dimensional refers to the fact that the sample mixture is partially resolved (in one dimension) using one separation technique, then the output from this first separation is further resolved (in the second dimension) using a second separation technique. The number of dimensions is equal to the number of separation techniques employed. The sample properties that determine sample separation in the first dimension should be different from those properties that determine sample separation in the second dimension in order to maximize separation resolution. If the sample properties that determine separation are totally different in both dimensions, the dimensions are said to be orthogonal. This is desirable since it enhances separation resolution.

An example of a two-dimensional separation is described by Liu and Le Van in U.S. Patent Application Publication U.S. 2002/0033336 A1. The first dimension is high-performance liquid chromatography (HPLC) and the second dimension is a plurality of electrophoresis columns. Liu and Le Van also disclose a separation where the first dimension is isoelectrical focusing and the second dimension is an array of capillary gel electrophoresis channels.

Another example of a two-dimensional separation is described by Wiktorowicz and Raysberg in U.S. Pat. No. 6,013,165. In one embodiment of the invention, the first dimension is gel electrophoresis to separate samples by size and charge and the second dimension is isoelectric focusing.

Akins in U.S. Patent Application Publication No. US 2002/0153252 A1 describes further examples of 2-dimensional systems in which the first dimension is cationic electrophoresis and the second dimension is one of denaturing electrophoresis, electrophoresis subsequent to proteolytic cleavage, isoelectric focusing non-equilibrium pH gel electrophoresis or immobilized pH gradient electrophoresis.

The present invention is an orthogonal two-dimensional system employing chromatofocusing (CF) as the first dimension and multiplexed capillary gel electrophoresis (MCGE) as the second dimension. These two dimensions are totally orthogonal, unlike some of the others above mentioned and, therefore, result in a higher degree of separation resolution.

For reasons not fully known to the inventors, no one has previously combined CF and MCGE as the two dimensions. Perhaps this is because they are relatively new techniques, their orthogonal nature has not been appreciated, and some of the buffer reagents used for each have been incompatible. Applicants have, however, discovered that the combination of CF and MCGE achieves good resolution in minimum time and can be used to advantage.

The widely accepted technique for protein analysis is traditional 2D gel electrophoresis. This is a method for the separation and identification of proteins in a sample by displacement in 2 dimensions oriented at right angles to one another. The first dimension is isoelectric focusing (IEF) which separates proteins according to isoelectric point (pI) differences while the second dimension is polyacrylamide gel electrophoresis (SDS-PAGE) which separates proteins according to their sizes.

However, there are many disadvantages related to the 2D gel electrophoresis. It is labor intensive, time consuming and poorly automated. Usually it takes several days to complete an analysis. Proteomics research requires the development of new techniques that have the following features: (1) increased resolving power and speed, (2) the ability to analyze proteins with varied properties (isoelectric points, molecular weights, hydrophobicities), (3) simplicity and automation and (4) the ability to perform high throughput analysis.

CF coupled with MCGE is a good alternative for the traditional 2D gel electrophoresis. It provides higher speed (it takes several hours to complete an analysis instead of several days in traditional 2D gel electrophoresis), automation and high throughput. The data output is directly comparable to the traditional 2D gel electrophoresis results.

CF is a form of ion-exchange chromatography. The objective of CF is to elute proteins from a column in order of their isoelectric points. An isoelectric point is the pH at which the net charge on a molecule in solution is zero. A weak anion (in anion CF) exchange column is equilibrated with a low ionic strength buffer at a high pH. The sample protein is loaded onto the column. Proteins are bound to the anion exchanger at the high pH. A pH gradient is then produced by adding a second, lower pH buffer. This buffer contains species that have a wide range of $pK_a$s. The range of $pK_a$s provides level buffer capacity across the entire pH range of the gradient. As the pH on the column decreases, protein positive charges become stronger and there is less interaction between the column and the protein. Eventually, the protein does not interact with the column and it elutes. The bound proteins are eluted in order of their isoelectric points, from high to low.

High performance MCGE has rapidly become an important analytical tool for the separation of a large variety of compounds ranging from small ions to large biological molecules. MCGE is used for general separations, enantiomeric separations, protein separations, the peptide mapping of proteins, amino acid analysis, nucleic acid fractionation and the quantitative measurement of acid dissociation constants ($pK_a$ values) and octanol-water partition coefficients (log $P_{ow}$ values).

What all these MCGE applications have in common is the measurement of the mobility of chemical species in a capillary tube as a means of identifying it. To perform a conventional separation, a capillary tube is filled with a buffer solution, a sample is loaded into one end of the capillary tube, both ends of the capillary tube are immersed in the buffer solution and a large potential is applied across the capillary tube. The sample components are separated electrophoretically as they migrate through the capillary tube. In a UV detection system, a section of capillary tube is irradiated with a UV light source. A photodetector detects the light that passes through the tube. When a UV absorbing sample component passes through the irradiated portion of the capillary tube, the photodetector detects less passed light (indicating absorbance). In this way an electropherogram, a plot of absorbance versus time, can be produced.

The rapid development of biological and pharmaceutical technology has posed a challenge for high-throughput analytical methods. For example, current development of combinatorial chemistry has made it possible to synthesize hundreds or even thousands of compounds per day in one batch. Characterization and analysis of such huge numbers of compounds has created a bottleneck. Parallel processing (i.e., simultaneous multi-sample analysis) is a natural way to increase the throughput. Unlike high-performance liquid chromatography or gas chromatography, it is practical to build a highly multiplexed CE instrument that can analyze dozens of samples simultaneously. Such a system has been disclosed in PCT Application WO 01/18528A1.

There is a continuing need for development of multidimensional separation techniques of high speed and high resolution. To date, no one has combined chromatofocusing (CF) and multiplexed capillary electrophoresis (MCGE). It is believed that this is because both techniques are relatively new; chromatofocusing was disclosed in 1978 and MCGE is even younger and because their orthogonal relationship has not heretofore been appreciated for use in two-dimensional techniques.

Another reason that CF and MCGE have not been combined for protein separation is that buffers used for CF often interfere with the absorption detection employed with MCGE. Protein absorbance is stronger at a wavelength of 214 nm than 280 nm. Therefore, 214 nm is preferred for MCGE detection systems because it allows greater sensitivity of detection. However, typical CF systems use absorbance detection for proteins at 280 nm. The reason is that the buffer used, commonly Polybuffer™ available from Amersham BioSciences, strongly absorbs at 214 nm. If Polybuffer™ is used in conjunction with a detection system at 214 nm, the absorbance distorts the baseline and hinders detection of proteins. In short, one reason the two techniques have not been combined is a lack of a buffer that will work well in both systems, preferably at 214 nm. The applicants have discovered such a buffer.

The applicants have discovered that multidimensional separations combining CF and MCGE as herein described have the advantage of being totally automatable, thus achieving certain labor efficiencies. Furthermore, it is advantageous to combine CF rather than isoelectric focusing, as has been done in the past, with MCGE. This is because CF has the capacity to handle large samples. This is beneficial to the second dimension, MCGE, for detection and separation. If the amount of sample from the first dimension is too low, there can be sensitivity problems in the second dimension.

Additionally, it is particularly advantageous to combine CF with MCGE because the output from CF is a large number of aliquots of solution. With MCGE, due to the multiplexing, all the aliquots can be analyzed simultaneously in separate capillary tubes.

The primary objective of the present invention is to design a two-dimensional, orthogonal separation technique that combines CF and MCGE to provide high speed and high resolution separations. The method and manner of achieving this primary objective as well as others will become apparent from the detailed description that follows.

BRIEF SUMMARY OF THE INVENTION

This invention relates to a two-dimensional system of separation and a method for separating sample components, particularly proteins. The first dimension is chromatofocusing and the second dimension is capillary gel electrophoresis. The invention is two-fold in its aspect: first is the integration of CF and MCGE for protein separation. Second, and complementary to the first, is a buffer appropriate for use in an integrated CF/MCGE system.

DETAILED DESCRIPTION OF THE PREFERRED EMBODIMENT

The invention, as hereinbefore explained, is a CF system integrated with an absorbance-based MCGE. The invention system and method are for the separation, detection and identification of chemical species, particularly proteins.

Figure 1:
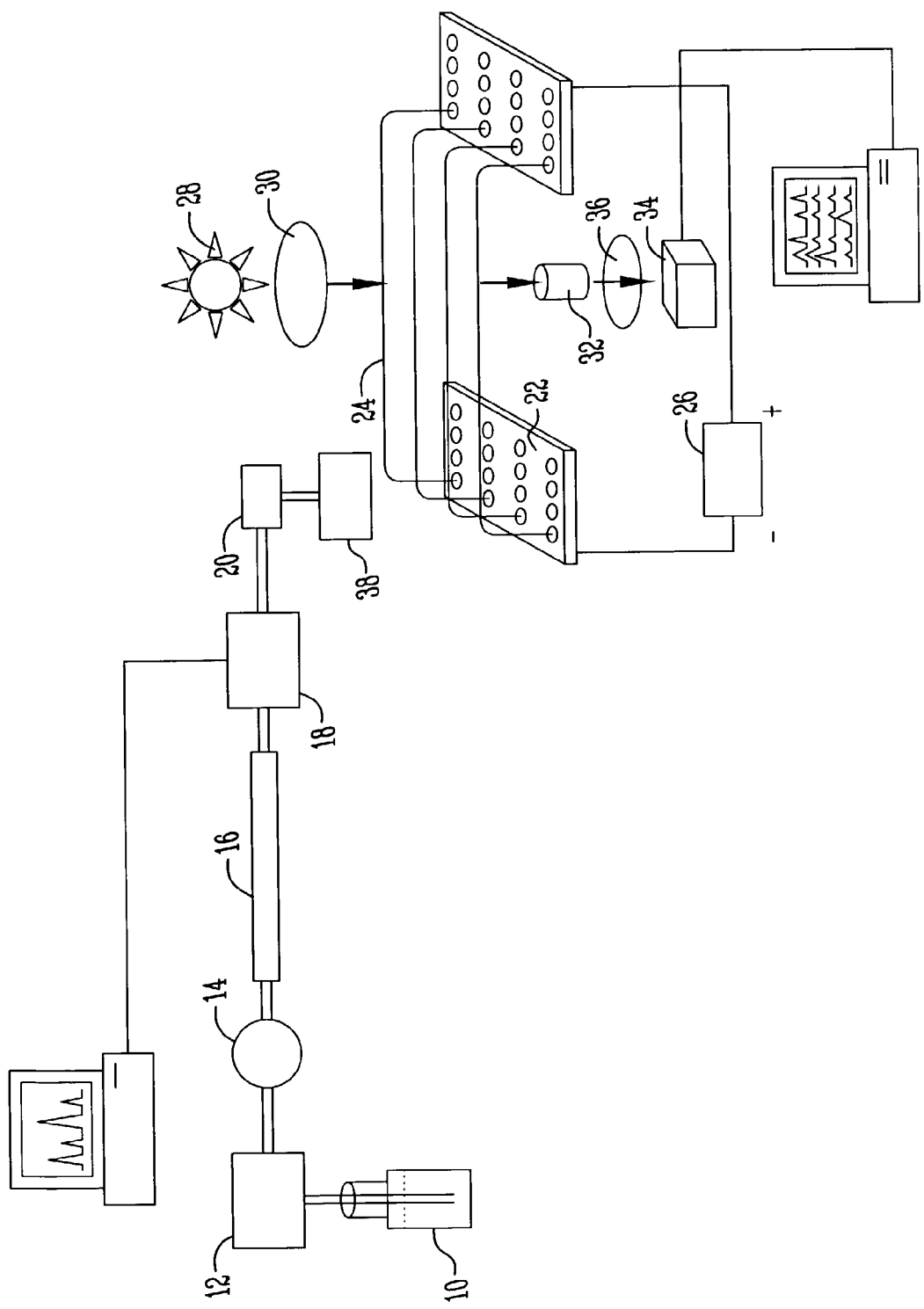
FIG. 1 presents a schematic diagram of a chromatofocusing system integrated with a multiplexed capillary electrophoresis system.

Refering to FIG. 1, the column 16 is initially equilibrated with a starting solution adjusted to high pH. After equilibration, the sample is injected into the column 16 through the sample injector 14. The sample injector 14 is the same as used in high performance liquid chromatography. After sample injection, the pump 12 pumps lower pH buffer solution 10 towards the column 16. The column 16 is filled with a weak anion exchange resin. The sample proteins are separated in the column according to isoelectric point. Past the column is the detector 18. The detector measures the light absorption of proteins at a given wavelength, preferably 214 nm. Next in line is the pH monitor 20 that measures the pH of the solution after it exits the column. The sample is then collected with a programmable sample handling system 38 that collects fractions during certain time intervals, if operated in time mode, in a 96-well titer plate. The sample handling system 38 also has the following functions: liquid handling including liquid reagent addition, and sampling positioning for introducing a sample into the MCGE system. After finishing the required sample treatment, the titer plate is sent into the MCGE system for the second dimension separation and analysis. The transfer of sample can be done by human interference, but preferably by a robot arm for complete automation between injection of the sample in CF and data analysis with MCGE.

The inlet ends of capillary tubes 24 are immersed in a buffer solution in the sample tray 22. Some of the buffer solutions also contain the fractions from the first dimension of the separation. The samples are loaded into the capillary tubes. A large potential difference is applied-across the capillary tubes 24 and the proteins are separated electrophoretically.

The light beam originates in the light source 28 and then travels through the collimating lens 30, the planar array of capillary tubes 24, the flat-field lens 32, the optical filter 36 and is collected in the detector. The protein samples are detected by light absorption when they pass through the capillary tubes in the area illuminated by the light source.

The distance between the area where light is emitted from the light source 28 and the planar array of capillary tubes 24 is not critical to the practice of the present invention. However, the shorter the distance between the area where light is emitted from the light source 28 and the planar array of capillary tubes 24, the more light is received by the planar array of capillary tubes. The more light that the planar array of capillary tubes receives, the more sensitive is the detection.

Preferably, the distance between the planar array of capillary tubes 24 and the detector 34 is at least about 10 times, more preferably, at least about 100 times, a cross sectional distance of a capillary tube measured orthogonally to the plane of the planar array of capillary tubes 24. The critical feature is that the distance must be such that the entire array is visible and in focus. Thus, the distance between the planar array of capillary tubes 24 and the detector 34 is preferably from about 1 centimeter to about 100 centimeters, more preferably from about 3 cm to about 40 centimeters, and most preferably from about 20 centimeters to about 40 centimeters.

By "capillary tubes" 24 is meant at least 3 or more, preferably at least about 10, more preferably at least about 90, and desirably as many as can be accomodated by the system described herein. The capillary tubes 24 allow the passage of light from the light source 28 through the walls of the capillary tubes 24 facing the light source 28, through the samples in the capillary tubes 24, and through the walls of the capillary tubes 24 facing the detector. Thus, the walls of the capillary tubes 24 are desirably transparent, although, in some instances, the walls of the capillary tubes 24 can be translucent. It is not necessary for the entirety of the walls of the capillary tubes 24 to allow the passage of light from the light source 28 as described above as long as at least a portion of the walls of the tubes allow the passage of light from the light source 28 such that the samples in the capillary tubes 24 are irradiated and light that is not absorbed by the absorbing species and samples is detectable by the detector.

In general, the capillary tubes 24 should have smooth surfaces and uniformly thick walls and be made of a material transparent over the range of wavelengths of light absorbed by an absorbing species in the sample, the absorbance of which is to be detected or measured. Preferred materials for capillary tubes 24 include, but are not limited to, plastics, quartz, fused silica and glass. The cross-section of a capillary tube 24 is not critical to the present invention. However, the smaller the cross-section of the capillary tube 24, the more useful is the capillary tube 24 in highly multiplexed applications as a greater number of capillary tubes 24 can be used in a smaller amount of space. Similarly, the thickness of a walls of the capillary tubes 24 is not critical to the present invention. The walls should be of sufficient thickness as to maintain the structural integrity of the capillary tube 24, yet not so thick as to adversely impede the passage of light through the capillary tube 24. The shape of the capillary tube 24 also is not critical to the present invention. The capillary tube 24 can have any suitable shape. However, the preferred size and shape of the capillary is 150 $\mu$m outside diameter, 75 $\mu$m inside diameter and circular in shape. Desirably, the shape of the capillary tube 24 is conducive to being closely packed and minimizes the generation of stray light by the container. The capillary tubes 24 are preferably from about 10 cm to about 200 cm long.

Capillary tubes 24 are commercially available by a number of sources including Polymicro Technologies, Inc., Phoenix, Ariz. The capillary tube 24 is preferably coated with a polymer such as polyimide so that it is mechanically stable. The coating must be removed in the region to be irradiated by the light source 28. An excimer laser can be used to remove the polymer coating.

Preferably, the capillary tubes 24 in the planar array are arranged substantially parallel and adjacent to each other. Adjacent capillary tubes 24 can be physically touching each other along all or a portion of their lengths, although slight inconsistencies in capillary wall diameter or other features of the array can prevent them from being in contact along their entire lengths.

The electrical potential used for electrophoretic separation is not critical to the invention. A typical potential generated by the high voltage power 26 supply ranges from 5,000 to 30,000 V.

If a large amount of heat is generated during the method, particularly in the vicinity of the planar array of capillary tubes 24, cooling should be employed to dissipate the heat. Excessive heat can lead to mechanical vibrations between adjacent capillary tubes 24, which, in turn, can lead to excess noise. Fans can cool the capillary tubes 24.

The detector 34 can comprise any suitable means of detecting absorption. Preferably, the detector 34 comprises a plurality of absorption detection elements, such as a plurality of photosensitive elements, which desirably are positioned in a linear array, although a two-dimensional image array detector can be used. Desirably, the detector 34 is parallel to and in-line with a linear array of capillary tubes 24. The detector 34 is desirably rigidly mounted to reduce flicker noise.

Preferably, the detector 34 is a linear photodiode array (PDA). Desirably, the PDA incorporates a linear image sensor chip, a driver/amplifier circuit and a temperature controller, which desirably thermoelectrically cools the sensor chip to a temperature from about 0° C. to about −40° C. Lowering the temperature lowers the dark count and minimizes the temperature drift, thus enabling reliable measurements to be made over a wide dynamic range. The driver/amplifier circuit is desirably interfaced to a computer via an I/O board, which preferably also serves as a pulse generator to provide a master clock pulse and a master start pulse, which are required by the linear image sensor. The PDA records the image linearly, not two-dimensionally. Preferably, the data acquired is written directly to the hard disk in real time. Also, preferably, the signals from up to at least 10 elements of the PDA are displayed in real time.

Preferably, the PDA comprises linearly aligned pixels, in which case each capillary tube is optically coupled to less than about 10 pixels, more preferably from about 7 to about 9 pixels, some of which are coupled to the walls of the capillary and at least one of which is coupled to the lumen of the capillary. A pixel exposed to light produces an electronic signal that is proportional to the intensity of incident light.

The light source 28 preferably emits light of a wavelength in the range from about 180 nm to about 1500 nm. Examples of a suitable light source 28 include mercury (for ultra violet (UV) light absorption), tungsten (for visible light absorption), iodine (for UV light absorption), zinc (for UV light absorption) cadmium (for UV light absorption), xenon (for UV light absorption) or deuterium (for visible light absorption) lamps. Desirably, the light source 28 emits a wavelength of light that will be absorbed by the species of interest. Which wavelength of light is absorbed by the species of interest can be determined using a standard absorption spectrometer. Alternatively, spectroscopic tables that provide such information are available in the art, such as through the National Institute of Science and Technology. Desirably, a maximally absorbed wavelength of light is selected for a given species to be detected or measured such that smaller amounts of the absorbing species can be detected. The light source 28 can be a point source. Also, preferably, the light source 28 has a power output of about 0.5 mW to about 50 mW.

An optical filter 36 is desirably positioned between the planar array of capillary tubes 24 and the detector 34. The optical filter 36 prevents stray light from the outside environment from reaching the detector 34. The filter 36 passes light at and near the wavelength emitted from the light source 28 and blocks light of other wavelengths.

A flat-field lens 32 is desirably positioned between the planar array of capillary tubes 24 and the detector 34. The flat-field lens 32 couples light that is not absorbed by the one or more absorbing species in each sample with the detector 34. While a lens that is not a flat-field lens can be used in the context of the present invention, it is disadvantageous in as much as it does not image the entire field evenly. Consequently, the edges of the field are distorted and the absorption of the capillary tubes 24 positioned at the edges of the field of the lens cannot be detected or measured. The flat-field lens 32 inverts the image of the planar array onto the face of the detector 34.

A collimating lens 30 is desirably positioned between the light source 28 and the planar array of capillary tubes 24. The collimating lens 16 focuses the light from the light source 28 to irradiate the capillary tubes 24 more effectively.

While the sample can be introduced into each capillary tube 24 in a planar array of multiple capillary tubes 24 by any suitable method, preferably the samples are introduced into the capillary tubes 24 by pressure, gravity, vacuum, capillary or electrophoretic action.

The above components are placed to eliminate substantially, and desirably, completely, stray light. There are two kinds of stray light. One kind of stray light is the glare that results from the capillary tubes 24 having sidewalls and interior lumens. The other kind of stray light is that which is due to the presence of other capillary tubes 24. This kind of stray light is referred to as "cross talk." Cross talk essentially is the glare from other capillary tubes 24. Thus, there needs to be sufficient distance between the sample and the flat-field lens 32 to eliminate substantially and, desirably completely the two kinds of glare. The rate of decrease of stray light as the distance increases will eliminate most of the glare from the containers. Glare can be assessed by measuring a totally absorbing material in a container. If there is any light detected, that light is due to glare.

Preferably, raw data sets are extracted into single-diode electropherograms and analyzed by converting the transmitted light intensities collected at the detector 34 to absorbance values using a capillary tube 24 containing only buffer solution as a continuous blank reference (control). Alternatively, as many as five and preferably three adjacent diodes may be summed for each capillary tube 24 of the array to increase the overall light intensity. Root-mean-squared noise in the electropherograms is obtained using a section of baseline near one of the analyte peaks. Mathematical smoothing can be used to reduce noise significantly, without distorting the signal. In this regard, as high a data acquisition rate as possible should be employed to provide more data points for smoothing. Various algorithms including binomial, boxcar and Savitzky-Golay smoothings are preferred methods of mathematical smoothing.

EXAMPLE 1

Separation of Egg White Proteins

The starting material was egg white. The starting solution was 25 mM diethanolamine adjusted to pH 9.5 with hydrochloric acid. The egg white was diluted with the starting solution to one fourth initial concentration and centrifuged at 13,400 rpm for 5 minutes. The supernatant was injected into a chromatofocusing column 16. The column 16 was a Mono P HR 5/20 from Pharmacia Biotech packed with Mono P, an anion exchange resin. The column 16 was equilibrated before sample injection with the starting solution. After sample injection, the column 16 was eluted with a solution 10 of 2 mM N-[2-Hydroxy-1,1-bis(hydroxymethyl)ethyl] glycine (tricine, $pK_a$=8.1), 2 mM 3-(Cyclohexylamino)-2-hydroxy-1-propanesulfonic acid (CAPSO, $pK_a$=9.6), 2 mM 3-(Cyclohexylamino)-1-propanesulfonic acid (CAPS, $pK_a$=10.4), 2 mM Iminodiacetic acid ($pK_a$=2.98), 2 mM Glycine ($pK_{a1}$=2.35, $pK_{a2}$=9.78), 2 mM 4-Morpholinepropanesulfonic acid (MOPS, $pK_a$=7.2), 2 mM 2-Morpholinoethanesulfonic acid (MES, $pK_a$=6.1), 2 mM tris(hydroxymethyl)aminomethane (Tris, $pK_a$=8.3), 2 mM 2-[(2-Hydroxy-1, 1-bis(hydroxymethyl)ethyl)amino]ethanesulfonic acid (TES, $pK_a$=7.4), 2 mM Alanine, 2 mM 4-(2-Hydroxyethyl)piperazine-1-ethanesulfonic acid (HEPES, $pK_a$=7.5), 2 mM N-(2-Hydroxyethyl)piperazine-N'-(3-propanesulfonic acid) (EPPS, $pK_a$=8.0), 2 mM N-(2-Acetamido)-2-aminoethanesulfonic acid (ACES, $pK_a$=6.8), 2 mM N-(1,1-Dimethyl-2-hydroxyethyl)-3-amino-2-hydroxypropanesulfonic acid (AMPSO, $pK_a$=9.0), 2 mM 2 -(Cyclohexylamino)ethanesulfonic acid (CHES, $pK_a$=9.3), 2 mM [(2-Hydroxy-1,1-bis(hydroxymethyl)ethyl)amino]-1-propanesulfonic acid (TAPS, $pK_a$=8.4), 2 mM 1,1,1,3,3,3-Hexakis(dimethylamino)diphosphazenium tetrafluoroborate (Bis-Tris) and 2 mM arginine ($pK_{a1}$=1.82, $pK_{a2}$=8.99), adjusted to pH 3.5 with 10% acetic acid.

Figure 2:
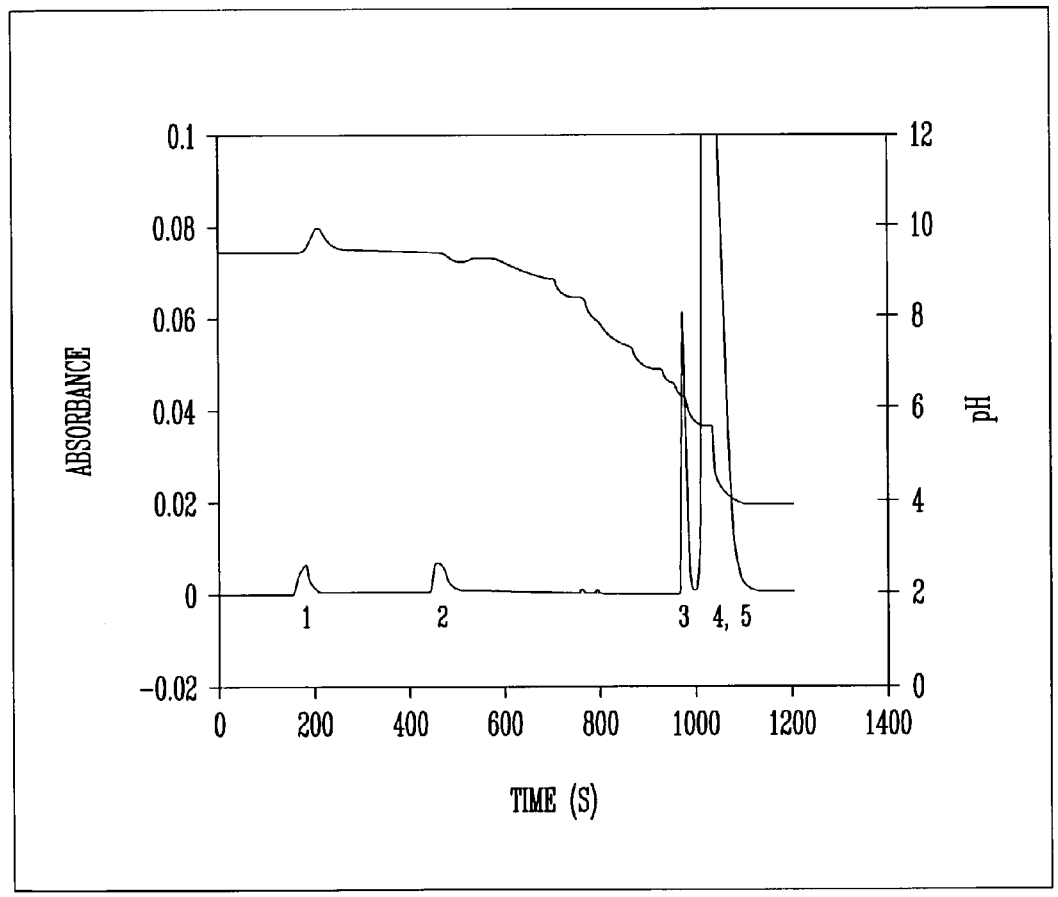
FIG. 2 shows the output from a chromatofocusing column for an eggwhite sample.

FIG. 2 shows the output from the chromatofocusing column 16. The pH of the solution exiting the column and the absorbance (at 280 nm) of any species are monitored as a function of time. Five different fractions were collected, one fraction each for the small absorbance peaks labelled 1, 2 and 3 and two fractions, 4 and 5, for the large absorbance peak.

The fractions collected from the chromatofocusing instrument were electrokinetically injected into the capillaries 24 of the MCGE system. Separations were performed at 15 kV with a running time of 30 min.

Figure 3:
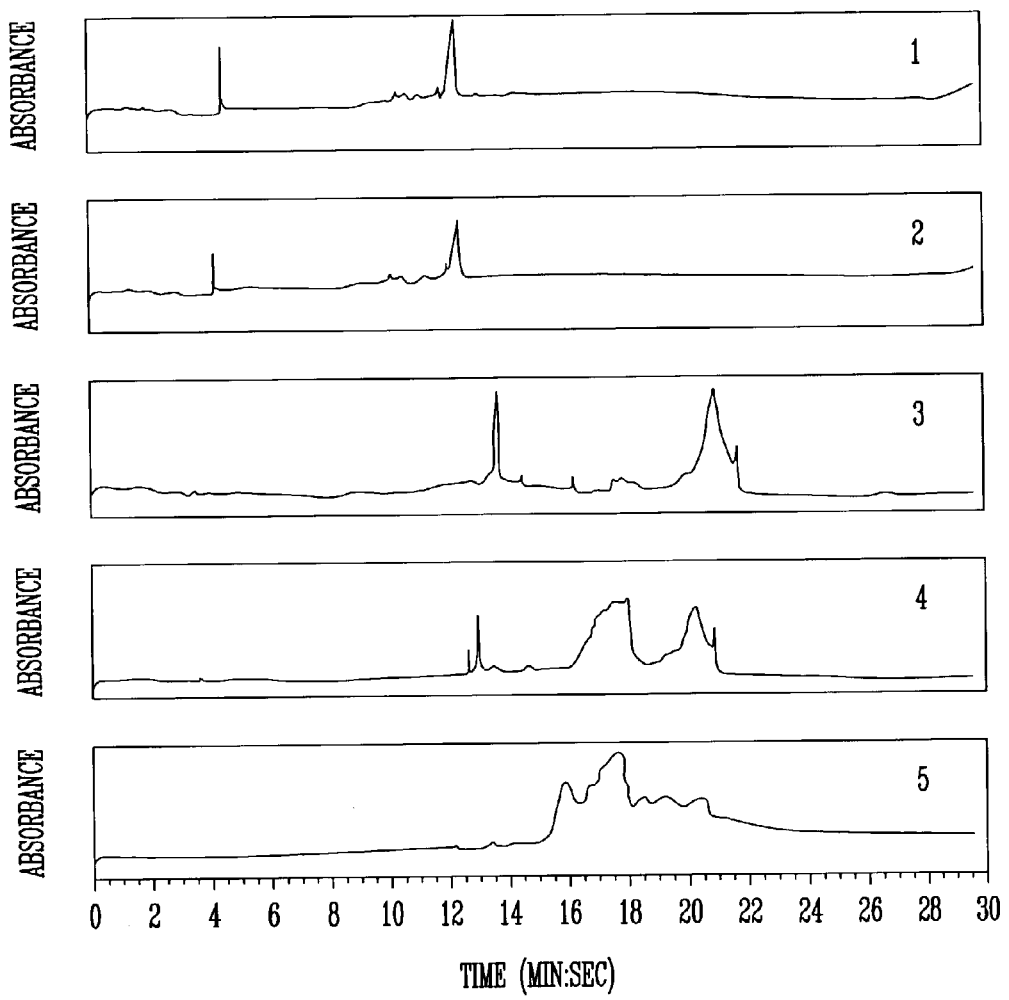
FIG. 3 shows electropherograms obtained simultaneously for five chromatofocussing fractions.

FIG. 3 shows electropherograms obtained simultaneously for the five fractions. All electropherograms show further resolution of egg white proteins than was achieved by chromatofocusing alone. For example, what is one protein absorbance peak in fraction 3 is further resolved into one large, one medium and several small peaks, all corresponding to different proteins, in electropherogram 3.

From the above description it can be seen that the invention works, provides a valuable separation system and accomplishes the stated objectives.

What is claimed is:

1. A two-dimensional protein separation method comprising:
    obtaining a test sample suspected of containing a plurality of proteins;
    buffering the test sample with a suitable integrated buffer usable in both chromatofocussing and multiplexed capillary electrophoresis,
    treating the sample with a chromatofocusing system to produce a first separated protein sample; and thereafter
    treating at least a portion of the first separated protein test sample with multiplexed capillary electrophoresis to produce a second separated protein sample; and
    determining from the combination of chromatofocusing and multiplexed capillary electrophoresis the protein content of the sample.

2. The method of claim 1 wherein the buffer is compatible with multiplexed capillary electrophoresis system set for absorbance detection at about 214 nm 3. A protein separation apparatus comprising:
    a chromatofocusing system for producing separated protein samples at an output;
    a multiplexed capillary electrophoresis system having inputs for receiving protein samples; and
    wherein the output of the chromatofocusing system is the input to the multiplexed capillary electrophoresis system such that the separated protein samples are from the chromatofocusing system are further separated by the multiplexed capillary electrophoresis system.

* * * * *